United States Patent [19]

Nauta

[11] 3,991,063
[45] Nov. 9, 1976

[54] AMINOISOQUINOLINES

[76] Inventor: Wijbe Thomas Nauta, Nieuw Loosdrechtsedijk 233, Nieuw Loosdrecht, Netherlands

[22] Filed: Feb. 3, 1975

[21] Appl. No.: 546,747

Related U.S. Application Data

[63] Continuation of Ser. No. 286,879, Sept. 7, 1972, abandoned.

[30] Foreign Application Priority Data

Sept. 9, 1971  United Kingdom............... 42143/71

[52] U.S. Cl.................... 260/288 D; 260/283 SY; 260/288 CE; 424/258
[51] Int. Cl.²..................................... C09D 217/22
[58] Field of Search................. 260/288 D, 288 CE

[56] References Cited
UNITED STATES PATENTS

| | | | |
|---|---|---|---|
| 3,277,085 | 10/1966 | Aebi et al. ...................... | 260/288 D |
| 3,702,849 | 11/1972 | Cronin et al..................... | 260/288 D |
| 3,758,480 | 9/1973 | Reimlinger et al. ............ | 260/288 D |
| 3,775,417 | 11/1973 | de Ruiter et al................ | 260/288 D |

FOREIGN PATENTS OR APPLICATIONS

| | | | |
|---|---|---|---|
| 1,573,135 | 4/1968 | France............................. | 260/288 D |
| 6,808,726 | 6/1968 | Netherlands.................... | 260/288 D |

*Primary Examiner*—Nicholas S. Rizzo
*Assistant Examiner*—Mary C. Jaughn
*Attorney, Agent, or Firm*—Robert E. Burns; Emmanuel J. Lobato; Bruce L. Adams

[57] ABSTRACT

New amino-isoquinoline derivatives of the general formula:

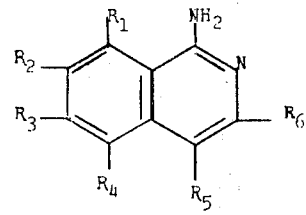

wherein $R_1$ and $R_4$ are the same or different and each represents a hydrogen or halogen atom or an alkyl group, $R_2$ and $R_3$ are the same or different and each represents a hydrogen or halogen atom or an alkyl or alkoxy group or $R_2$ and $R_3$ together represent a methylenedioxy radical, $R_5$ represents a hydrogen atom or an alkyl or aryl group and $R_6$ represents a di (lower alkyl) amino group or a nitrogen containing 5- or 6-membered heterocyclic radical linked to the isoquinoline nucleus either through a carbon atom or through the nitrogen atom such as 2-, 3- or 4-pyridyl, or 1-pyrrolidinyl are described. The aforesaid alkyl and alkoxy groups are preferably lower alkyl and lower alkoxy groups respectively. By the terms "lower alkyl" and "lower alkoxy" as used in this specification are meant straight or branched chain alkyl and alkoxy groups respectively having at most 6 carbon atoms. The preferred aryl group, which may be represented by $R_5$, is phenyl. The compounds appear effective in respiratory or oxidative processes in living organisms. When $R_6$ contains certain nitrogen moieties such as dialkylamino, and certain nitrogen heterocycles are effective economic poisons i.e. rodenticides, bacteriocides and fungicides. In less than toxic doses, the compounds are useful in combatting Chronic Respiratory Disease in poultry and in combatting barbiturate-induced respiratory failure.

5 Claims, No Drawings

AMINOISOQUINOLINES

This is a continuation of application Ser. No. 286,879, filed Sept. 7, 1972, now abandoned.

This invention relates to aminoisoquinolines and acid addition and quaternary ammonium salts thereof, to their preparation, and to compositions containing them.

According to the present invention, there are provided the new amino-isoquinoline derivatives of the general formula:

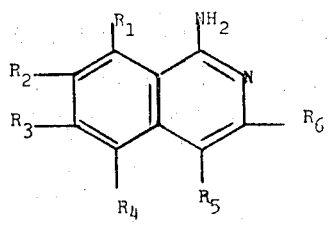

wherein $R_1$ and $R_4$ are the same or different and each represents a hydrogen or halogen atom or an alkyl group, $R_2$ and $R_3$ are the same or different and each represents a hydrogen or halogen atom or an alkyl or alkoxy group of $R_2$ and $R_3$ together represent a methylenedioxy radical, $R_5$ represents a hydrogen atom or an alkyl or aryl group and $R_6$ represents a di(lower alkyl)amino group or a nitrogen containing 5- or 6-membered heterocyclic radical linked to the isoquinoline nucleus either through a carbon atom or through the nitrogen atom such as 2-, 3- or 4-pyridyl, or 1-pyrrolidinyl. The aforesaid alkyl groups within the definition of $R_1$, $R_2$, $R_3$ and $R_4$ are preferably lower alkyl groups. The aforesaid alkoxy groups are preferably lower alkoxy groups. By the terms lower alkyl and lower alkoxy as used in this specification are meant straight or branched chain alkyl and alkoxy groups respectively having at most 6 carbon atoms. The preferred aryl group which may be represented by $R_5$ is phenyl.

The aminoisoquinolines of formula I in which $R_6$ is a di(lower alkyl) amino group are highly toxic substances which can be used as, for example, rodenticides. Those compounds in which $R_6$ is a nitrogen-containing heterocyclic radical posses useful bactericidal and fungicidal activities, for example against *Bacillus subtilis*, *Staphylococcus aureus*, *Streptococcus haemelyticus*, *Diplococcus pneumonia*, *Haemophilus influenzae*, *Mycoplasma gallisepticum*, *Pasteurella multocida*, *Shigellequirulis*, *Trichophyton mentagrophytes*, *Trichophyton rubrum* and *Candida albicans*. The most pronounced activity against the abovementioned bacteria and fungi is found in those compounds in which $R_6$ is a 2-pyridyl group, e.g. 1-amino-3-(2-pyridyl)-isoquinoline or 1-amino-3-(2-pyridyl)-4-undecylisoquinoline. The latter compounds are in particular very active against mycoplasmas, such as *Mycoplasma gallisepticum*, *Mycoplasma suipneumoniae* and *Mycoplasma synoviae*, the causative agents of respectively chronic respiratory disease in poultry, chronic pneumonia in swines and synovitis in poultry. The compound 1-amino-3-(2-pyridyl)isoquinoline also shows a pronounced activity against *Mycoplasma fermentans*. Activity against *Mycoplasma suipneumoniae* is also found in compounds in which $R_6$ represents a 4-pyridyl group, such as 1-amino-3-(4-pyridyl)isoquinoline.

Certain of the aminoisoquinolines of formula I, e.g. 1-amino-3-(4-pyridyl)isoquinoline dihydrochloride and 1-amino-3-(1-pyrrolidinyl)-isoquinoline monohydrochloride, have a respirative analeptic effect and may thus be used to recommence respiration, for example after an arrest due to barbiturate poisoning.

The compounds of formula I may be used as bases or as acid addition salts. Acid addition salts used for therapeutic purposes should contain pharmaceutically acceptable non-toxic anions, e.g. the hydrohalides, sulphates, oxalates, tartrates, fumarates, acetates, citrates, maleates, succinates, lactates and pamoates.

The aminoisoquinolines of formula I are prepared by reacting a nitrile of the formula:

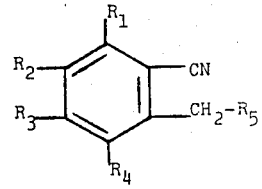

(wherein $R_1$, $R_2$, $R_3$, $R_4$ and $R_5$ are as hereinbefore defined) with a nitrile of the formula:

$$NC-R_6 \qquad\qquad III$$

(wherein $R_6$ is as hereinbefore defined) in the presence of a basic alkali metal-containing compound. Preferred alkali metal-containing compounds are amides or dialkylamides, such as sodium or potassium amide or lithium (diisopropyl) amide. The reaction is preferably carried out by keeping a mixture of the reactants in an inert organic solvent, or when the alkali metal-containing compound is an alkali metal amide, in liquid ammonia, under an inert gas atmosphere for several hours without heating. Suitable inert organic solvents are, for example, ethers such as diethyl ether or tetrahydrofuran. The temperature at which the reaction is carried out depends mainly on the alkali metal compound used. When, for example, lithium (diisopropyl)amide is employed, the reaction is generally carried out at room temperature, but when an alkali metal amide dissolved in liquid ammonia is used, the reaction temperature used is generally lower.

The starting materials of formulae II and III are known compounds or they can be prepared by methods known per se for the preparation of organic nitriles. By the term "methods known per se" as used herein is meant methods heretofore practiced or described in the chemical literature.

Acid addition and quaternary ammonium salts of the aminoisoquinolines of formula I may be prepared by methods known per se. For example, the base may be treated with the equivalent amount of the acid in an inert solvent to obtain the corresponding acid addition salt, or the base may be treated with the equivalent amount of an appropriate alkyl halide or dialkyl sulphate in a solvent having a high dielectric constant, for example acetonitrile, to obtain the quaternary ammonium salt.

The compounds of formula I generally react as monoacid bases when the nitrogen atom of $R_6$ is directly linked to the isoquinoline nucleus and as diacid bases in other cases. However, as can be seen in Example 1, exceptions to this rule may sometimes occur.

The following Examples illustrate the invention.

EXAMPLE 1

To 250 ml. of liquid ammonia under a nitrogen atmosphere are added 7.5 g. (0.19 gram atom) of potassium in small portions and a few crystals of ferric nitrate. When all the potassium has been converted into the amide (i.e. when the blue color disappears), 11.1 g. (0.095 mole) of o-toluonitrile in 30 ml. of anhydrous tetrahydrofuran are added, upon which the solution immediately takes on a red color. 19.8 g. (0.19 mole) of 2-cyanopyridine in 100 ml. of anhydrous tetrahydrofuran are then added. The mixture is left standing overnight and then decomposed with water. The tetrahydrofuran is evaporated and the residue is extracted with chloroform. The extract is washed with water, dried with magnesium sulphate and the solvent is removed by evaporation. The residue is purified by sublimation. 5.2 g. of 1-amino-3-(2-pyridyl)isoquinoline are obtained. Yield 24.8%, m.p. 152°–153° C. The base is dissolved in diethyl ether and an etheral hydrogen chloride solution is added. The precipitate formed is filtered off and crystallised from ethanol (96%) to yield the monohydrochloride, m.p. 266° C., (with decomposition). 0.95 g. (4.30 mmol) of the base and 2.44 g. (17.2 mmol) of methyl iodide, dissolved in 20 ml of acetone are heated at 43° C under a nitrogen atmosphere for 4 days. The solvent is distilled off and the residue is crystallised from methanol. 1-Amino-3-(2-pyridyl)isoquinoline methyliodide is obtained. Melting point 206° C with decomposition.

EXAMPLE 2

To 250 ml. of liquid ammonia under a nitrogen atmosphere are added 7.5 g. (0.19 gram atom) of potassium in small portions and a few crystals of ferric nitrate. When all the potassium has been converted into the amide, 11.1 g. (0.095 mole) of o-toluonitrile in 30 ml. of anhydrous tetrahydrofuran are added, and the solution immediately takes on a red color. 19.8 g. (0.19 mole) of 3-cyanopyridine in 100 ml. of anhydrous tetrahydrofuran are added, the mixture is left standing overnight and is then decomposed with water. The tetrahydrofuran is evaporated and the residue is extracted with diethyl ether. The extract is washed with water and dried with magnesium sulphate, and then an ethereal hydrogen chloride solution is added. The precipitate is filtered off and crystallised from a mixture of ethanol and water. There are obtained 500 mg. of 1-amino-3-(3-pyridyl)isoquinoline dihydrochloride, m.p. 247°–250° C. (with decomposition). The salt is dissolved in water as much as possible and then an excess of sodium hydroxide and diethyl ether are added. The mixture is stirred vigorously until all the solid has disappeared. The ethereal layer is separated and the solvent is evaporated. The residue is crystallised from petroleum ether (boiling range 80°–100° C) (A mixture of petroleum ether and chloroform may also be used). Melting point of the base 138°–139° C.

EXAMPLE 3

Using the procedure described in Example 2 but substituting an equivalent amount of 4-cyanopyridine for the 3-cyanopyridine there is obtained 1-amino-3-(4-pyridyl)isoquinoline dihydrochloride. The salt is crystallised from a mixture of methanol and diethyl ether. Yield 13.0%, m.p. 275° C. (with decomposition). The melting point of the base (obtained from the salt in a similar manner to that described in Example 2) is 168°–170° C. 0.95 g. (4.30 mmol) of the base and 2.44 g. (17.2 mmol) of methyl iodide, dissolved in 20 ml of acetone are heated at 43° C under a nitrogen atmosphere for 18 hours. The precipitate formed is filtered off and crystallised from methanol. 1-Amino-3-(4-pyridyl)isoquinoline methyl iodide is obtained. Melting point 266° C with decomposition.

EXAMPLE 4

To 250 ml. of liquid ammonia under a nitrogen atmosphere are added 7.5 g. (0.19 gram atom) of potassium in small portions and a few crystals of ferric nitrate. When all the potassium has been converted into the amide, 11.1 g. (0.095 mole) of o-toluonitrile in 30 ml. of anhydrous tetrahydrofuran are added, upon which the solution immediately takes on a red color. Then 13.3 g. (0.19 mole) of dimethylcyanamide dissolved in anhydrous diethyl ether are added. The mixture is left standing overnight and is then decomposed with water. The organic layer is separated off, washed with water and dried with magnesium sulphate. An etheral hydrogen chloride solution is then added which causes precipitation of the monohydrochloride of 1-amino-3-dimethylaminoisoquinoline. The salt is crystallized several times from 96% ethanol. Yield 39.2%, m.p. 255° C. (with decomposition.).

EXAMPLE 5

Using the procedure described in Example 4, but substituting an equivalent amount of diethylcyanamide for the dimethylcyanamide, the monohydrochloride of 1-amino-3-diethylaminoisoquinoline is obtained. The salt is crystallized from isopropyl alcohol. Yield 34.2%, m.p. 220°–221° C. (with decomposition).

EXAMPLE 6

Using the procedure described in Example 4, but substituting an equivalent amount of 1-cyanopyrrolidine for the dimethylcyanmide, the monohydrochloride of 1-amino-3-(1-pyrrolidinyl)isoquinoline is obtained. The salt is crystallized from a mixture of isopropyl alcohol and ethanol. Yield 52.3%, m.p. 235° C. (with decomposition).

The ethereal hydrogen chloride solution used in the Examples is obtained by passing gaseous hydrogen chloride into diethyl ether cooled in a mixture of salt and ice until no further hydrogen chloride is taken up. To form the desired salt, this solution is added to the solution containing the base until no further precipitate is formed.

EXAMPLE 7

Using the procedure described in Example 1, but substituting an equivalent amount of o-dodecyl benzonitrile for the o-toluonitrile, the hydrochloride of 1-amino-3-(2-pyridyl)-4-undecylisoquinoline is obtained. Melting point 160° C with decomposition.

The invention includes within its scope pharmaceutical preparations containing, as the active ingredient, at least one of the compounds of formula I in which $R_6$ is a nitrogen-containing 5-or 6-membered heterocyclic radical, or a non-toxic acid addition or quaternary ammonium salt thereof, in association with a pharmaceutically acceptable carrier. The preparations may take any of the forms customarily employed for administration of therapeutic substances.

Tablets and pills may be formulated in the usual manner with one or more pharmaceutically acceptable diluents or excipients, for example lactose, starch, calcium sulphate, dicalcium phosphate, microcrystalline cellulose or formaldehyde-casein, and may also include disintegration agents, for example starch, sodium alginate, Aerosil, Esma-Spreng (methylene casein), sodium dioctyl sulphosuccinate or potassium bicarbonate, lubricant materials, for example calcium or magnesium stearate, Precirol (a mixture of glycerol palmitate and stearate), stearic acid, talcum or polyethylene glycol, or binding agents, for example gelatin, polyvinylpyrrolidone, or cellulose derivatives such as methyl cellulose. Capsules made of absorbable material, such as gelatin, may contain the active substance alone or in admixture with a solid or liquid diluent.

Liquid preparations for oral use may be in the form of suspensions, emulsions, syrups or elixirs of the active substance in a liquid medium commonly used for making orally acceptable pharmaceutical formulations, such as vegetable oils, for example olive oil, arachis or sesame oil, polysorbates, propylene glycol, polyethylene glycol, glycerol, or a syrup or elixir base.

The active substance may also be made up in a form suitable for parenteral administration, i.e. as a suspension or emulsion in sterile water or any organic liquid commonly employed for injectable preparations, for example a vegetable oil such as olive oil or an organic solvent. The active substance may also be used in the form of preparations for topical application such as salves, ointments, lotions or powders, containing the usual excipients. Ointments may, for instance, contain semi-solid ointment bases such as vaseline or lanolin and emulsifying agents such as cetostearyl alcohol. In powders, the active substance may be mixed with finely divided solid substances such as talc or boric acid.

The dosage and mode of administration will depend on the mammalian species and the disease to be treated. In adult humans the daily oral dosage will be from 25 to 300 mg./kg. of body weight. For topical application, e.g. in the treatment of skin diseases, preparations such as salves, ointments, lotions or powders, containing from 0.5 to 5%, preferably 1 to 2%, by weight of the active substance may be used. Example VII illustrates a pharmaceutical preparation according to the invention.

EXAMPLE 8

A basis granulate is prepared from the following ingredients:

| | |
|---|---|
| lactose | 800 g. |
| potato starch | 200 g. |
| 5% aqueous potato starch solution | 200 ml. |

These ingredients are mixed, granulated and dried at 50° C. The mixture is passed through a sieve of 25 mesh. For the preparation of tablets weighing 250 mg. the following ingredients are used:

| | |
|---|---|
| 1-amino-3-(2-pyridyl)isoquinoline monohydrochloride | 100 mg. |
| basis granulate | 140 mg. |
| talcum | 8 mg. |
| magnesium stearate | 2 mg. |

The ingredients are passed through a sieve of 50 mesh, mixed and compressed into tablets in the usual manner.

The compounds of formula I in which $R_6$ is a 2-pyridyl or 4-pyridyl group, when used for combatting mycoplasma infections in animals, are suitably administered with the fodder in a concentration of 200 to 500 mg/kg of body weight.

The invention also includes within its scope rodenticidal preparations containing, as the active ingredient, at least one of the compounds of formula I in which $R_6$ is a di(lower alkyl) amino group or an acid addition or quaternary ammonium salt thereof, in association with a carrier generally used for rodenticides. The compounds may be mixed with, for example, baits such as meat, grain, mash and other known edible materials, fillers or carriers such as starch or kaolin. The final composition may be in a form customarily employed for this purpose, such as solutions, suspensions, pastes, powders or tablets. The concentration of the active compound in the compositions may vary from 0.5 to 10%, preferably 1 to 3%.

I claim:
1. Amino-isoquinoline compounds of the formula

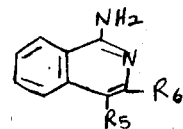

wherein $R_5$ represents a hydrogen atom or an alkyl or monocyclic carbocyclic aryl group and $R_6$ represents a di (lower alkyl) amino group, a pyridyl group, or a pyrrolidino group, said alkyl and lower alkyl groups each having up to 6 carbon atoms, and their acid addition and the lower alkyl sulfate and halo quaternary ammonium salts.

2. The amino-isoquinoline according to claim 1, 1-amino-3-(2-pyridyl)isoquinoline and its acid addition and lower alkyl sulfate and halo quaternary ammonium salts.

3. 1-amino-3-(2-pyridyl)-4-undecylisoquinoline and its acid addition and lower alkyl sulfate and halo quaternary ammonium salts.

4. The amino-isoquinoline according to claim 1, 1-amino-3-(4-pyridyl)isoquinoline and its acid addition and lower alkyl sulfate and halo quaternary ammonium salts.

5. The amino-isoquinoline according to claim 1, 1-amino-3-(1-pyrrolidinyl)isoquinoline and its acid addition and lower alkyl sulfate and halo quaternary ammonium salts.

* * * * *